(12) United States Patent
Hsu Huang et al.

(10) Patent No.: US 11,218,801 B1
(45) Date of Patent: Jan. 4, 2022

(54) POINT-PRESSED AUDIO PICKUP APPARATUS

(71) Applicant: JAZZ HIPSTER CORPORATION, New Taipei (TW)

(72) Inventors: Yueh-Hua Hsu Huang, New Taipei (TW); Lien-Huang Yang, New Taipei (TW)

(73) Assignee: Jazz Hipster Corporation, New Taipei (TW)

( * ) Notice: Subject to any disclaimer, the term of this patent is extended or adjusted under 35 U.S.C. 154(b) by 0 days.

(21) Appl. No.: 17/198,958

(22) Filed: Mar. 11, 2021

(51) Int. Cl.
*H04R 1/46* (2006.01)
*H04R 1/08* (2006.01)
*A61B 7/04* (2006.01)

(52) U.S. Cl.
CPC ............... *H04R 1/46* (2013.01); *A61B 7/04* (2013.01); *H04R 1/083* (2013.01)

(58) Field of Classification Search
CPC ............. H04R 1/46; H04R 1/083; A61B 7/04
See application file for complete search history.

(56) References Cited

U.S. PATENT DOCUMENTS

| 3,525,810 A * | 8/1970 | John | A61B 7/04 381/120 |
| 2020/0178924 A1* | 6/2020 | Hsu | A61B 5/0004 |

* cited by examiner

*Primary Examiner* — Andrew L Sniezek
(74) *Attorney, Agent, or Firm* — Muncy, Geissler, Olds & Lowe, P.C.

(57) ABSTRACT

A point-pressed audio pickup apparatus includes a deformation element and an audio pickup device. The deformation element is pushed by an external force to induce deformation, so that a distance sensing element in the audio pickup device can measure the deformation through the changed distance so as to trigger the audio pickup device to start receiving sound.

14 Claims, 9 Drawing Sheets

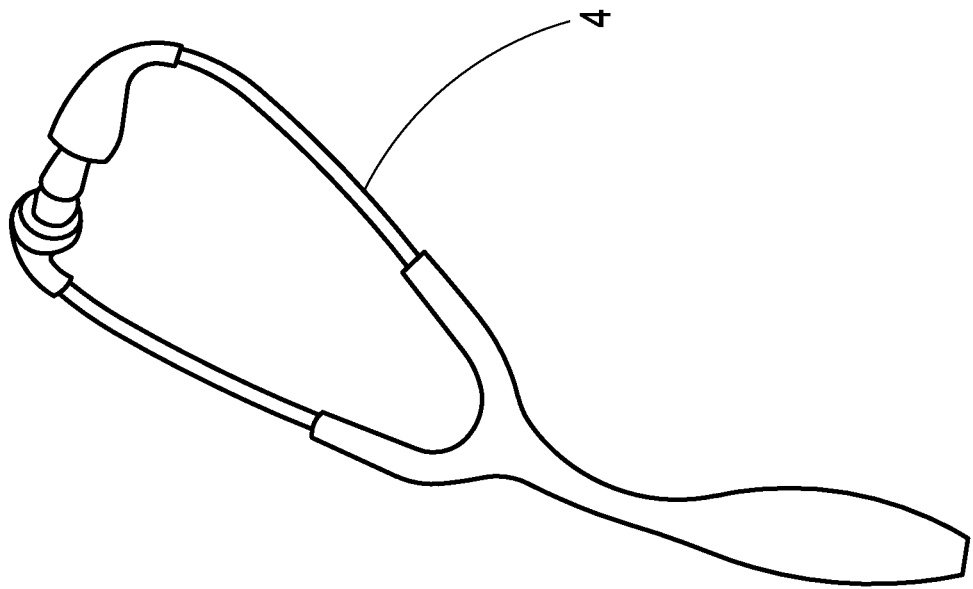
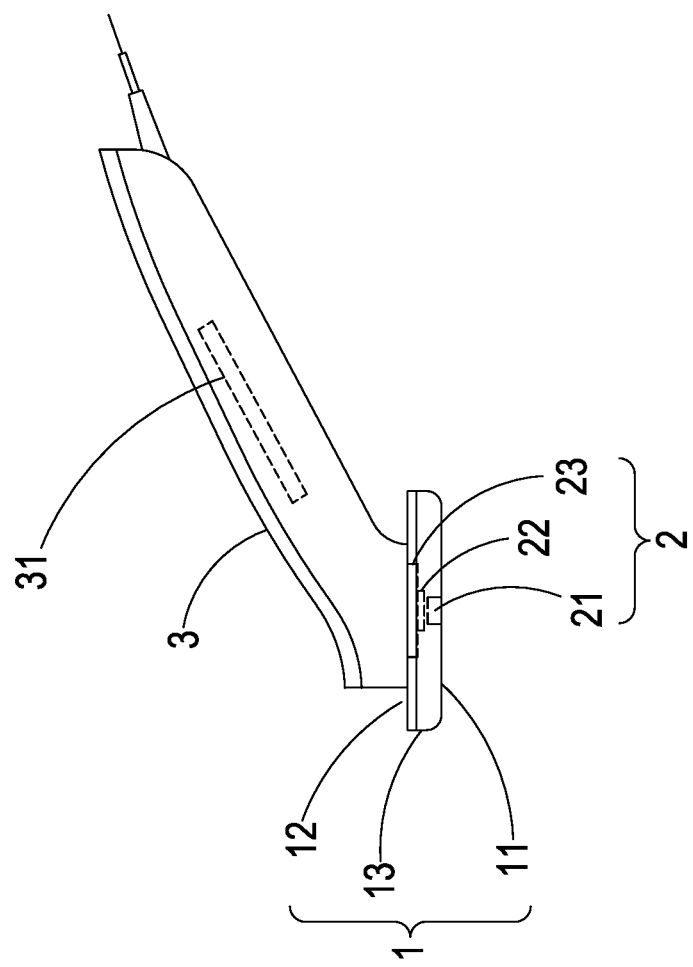
FIG. 1

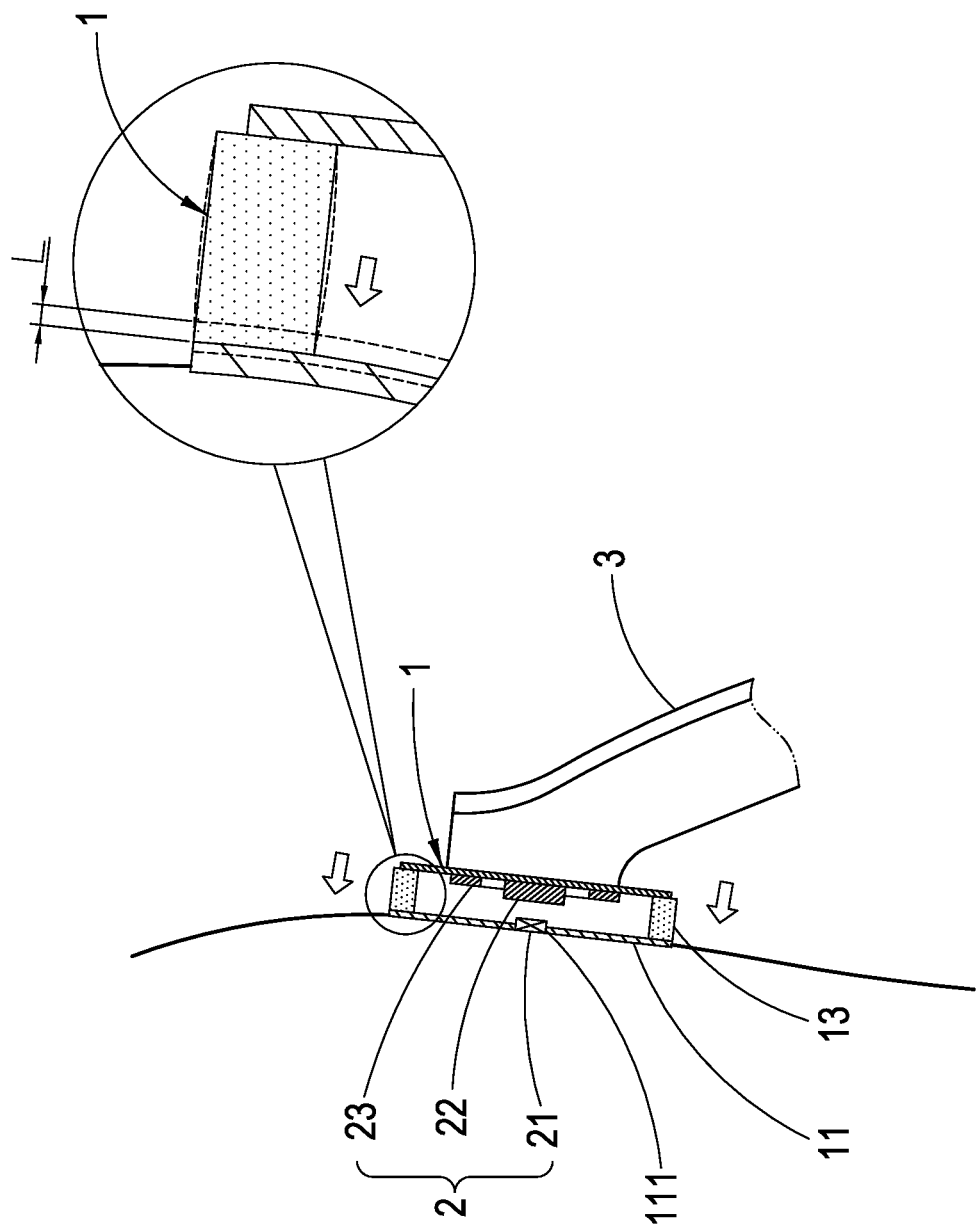

POINT-PRESSED AUDIO PICKUP APPARATUS

BACKGROUND OF THE INVENTION

1. Field of the Invention

The present invention relates to a point-pressed audio pickup apparatus applied to receive various physiological sounds (e.g., audio signals generated by the movement of heart, lungs, internal organs or internal tissues) thereby facilitating medical diagnoses.

2. Description of Related Art

It is well-known in conventional technologies that audio pickup devices can be used to receive various kinds of physiological sounds in the human body; in particular, the so-called stethoscope can be applied for medical purposes. Currently there are old-fashioned wired stethoscopes and wireless electronic stethoscopes, but no matter the wired stethoscope or the wireless electronic stethoscopes, they are mostly equipped internally with a contact-typed microphone in order to perform audio pickup when the stethoscope touches the human body.

However, during such sound pickup or reception processes, it is likely there may also exist certain rubbing sounds generated when the stethoscope moves or various environmental sounds during operations, and these unwanted noises may seriously affect the original physiological sounds and interfere with the medical staff for correct diagnoses. Therefore, the present invention provides a point-pressed audio pickup apparatus which adopts a type of point-pressures pickup method such that, as moving the audio pickup apparatus to a predetermined position, the user can receive the intended physiological sounds only when an external force is applied thereto at a single point so as to greatly reduce the noises generated during operations, thereby offering an effective solution for the aforementioned issues.

SUMMARY OF THE INVENTION

The present invention discloses a point-pressed audio pickup apparatus, comprising a deformation element and an audio pickup device, wherein the deformation element includes a first surface, a second surface and a joint block joined between the first surface and the second surface, in which any one or more of the first surface, the second surface and the joint block can induce deformation by an external force, and an audio pickup hole is openly configured at the central position of the first surface; the audio pickup device includes an audio pickup element installed inside the audio pickup hole, and a conduction element and a distance sensing element installed inside the deformation element, in which the audio pickup element and the distance sensing element are respectively electrically connected to the conduction element, and the distance sensing element is correspondingly installed by the side of the first surface; accordingly, the first surface is attached to the surface of an object in order to push or press the deformation element by an external force vertical to the first surface to induce deformation, such that the first surface or the second surface displaces in the vertical direction thereby reducing the distance between the first surface and the distance sensing element, so that the distance sensing element can operate to measure the distance length, and the audio pickup element will be triggered to receive sound when the measured distance length reaches more than 1 μm.

In a preferred embodiment, the deformation element is installed on an electronic device, the conduction element is also electrically connected to a control element within the electronic device, and the control element is further electrically connected to a sound playback device.

In a preferred embodiment, the distance sensing element and the conduction element are both installed on the second surface, and the distance sensing element corresponds to the first surface.

In a preferred embodiment, any one or more of the first surface, the second surface and the joint block are fabricated with flexible materials.

In a preferred embodiment, any one or more of the first surface, the second surface and the joint block are designed to have continuous bumpy wave forms, the extension directions of the continuous bumpy forms of the first surface and the second surface are parallel to the first surface, and the extension direction of the continuous bumpy forms of the joint block is vertical to the first surface.

In a preferred embodiment, the first surface, the second surface or the joint block designed to have continuous bumpy wave forms are fabricated with flexible materials.

In a preferred embodiment, the first surface designed to have a continuous bumpy wave forms has a protrusion formed towards outside.

In a preferred embodiment, any one or more of the first surface or the second surface are openly configured with a plurality of holes at the same time.

In a preferred embodiment, the first surface or the second surface openly configured with a plurality of holes are fabricated with flexible materials.

In a preferred embodiment, the flexible materials may be silicone, rubber, soft rubber, foam, sponge, springs or other materials capable of enabling deformability and automatically returning to the original shape thereof.

BRIEF DESCRIPTION OF THE DRAWINGS

FIG. 1 shows an overall structural stereo view of the point-pressed audio pickup apparatus according to the present invention.

FIG. 2 shows a structural cross-sectioned view of the point-pressed audio pickup apparatus according to the present invention.

DETAILED DESCRIPTION OF THE PREFERRED EMBODIMENTS

Figure 3A:
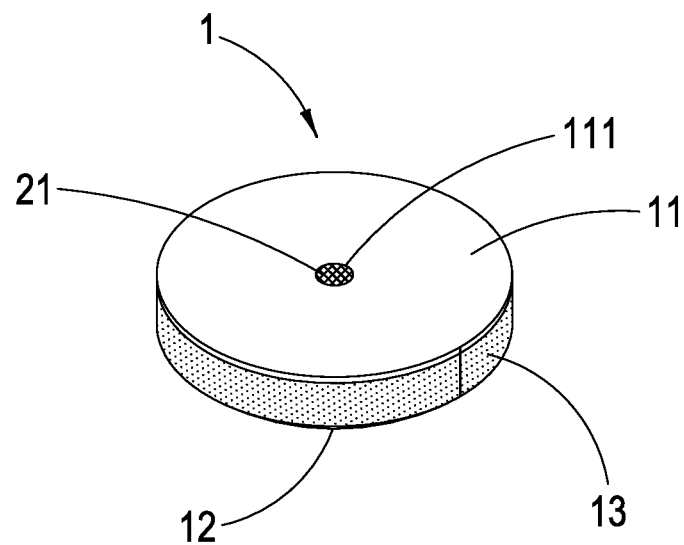
FIG. 3A shows a stereo view for a first embodiment of the deformation element in the point-pressed audio pickup apparatus according to the present invention.

Other technical contents, aspects and effects in relation to the present invention can be clearly appreciated through the detailed descriptions concerning the preferred embodiments of the present invention in conjunction with the appended drawings.

It should be appreciated that the term "on" used to describe the position of the structure disclosed in the contents of the present specification refers to any surface position of the structure, not commonly known as the directional terms, e.g., "on top of", "above", etc. Meanwhile, the terms "above" and "below" used to describe the position of the structure refer to the directionality of the position of the structure under common usage.

In addition, the terms "connection", "installation" or "setup" disclosed in the contents of the present specification for describing the combination relationship of the structure generally refer that multiple structures, after combination processes, will not easily fall apart or drop down, and such connections or combinations may comprise a fixed connection, a detachable connection, or an integrally formed connection; also, it may be a mechanical connection or an electrical connection; besides, it may be a directly physical connection or an indirectly physical connection through an intermediate medium, or otherwise an internal communication of two elements by using, e.g., threads, latches, fasteners, nails, adhesives or high frequency waves or any other feasible approaches.

Moreover, the terms "connection" or "electrical connection" disclosed in the contents of the present specification for describing the structural combination relationship refer to the combination of electric power enabling or network communications by using e.g., wires, circuit boards, network cables or wireless networks or any other feasible approaches.

Now, refer to FIGS. 1 and 2, wherein a stereo view and an internal structure cross-sectioned view of the point-pressed audio pickup apparatus according to the present invention are respectively shown, and it can be seen from such Figures that it comprises a deformation element 1 and an audio pickup device 2.

Herein the illustrated deformation element 1 includes a first surface 11, a second surface 12 and a joint block 13 joined between the first surface 11 and the second surface 12, in which any one or more of the first surface 11, the second surface 12 and the joint block 13 can induce deformation by applying an external force, and an audio pickup hole 111 is also openly configured at the central position of the first surface 11.

Meanwhile, the audio pickup device 2 includes an audio pickup element 21 installed inside the audio pickup hole 111, and a conduction element 22 and a distance sensing element 23 installed inside the deformation element 1, in which the audio pickup element 21 and the distance sensing element 23 are respectively electrically connected to the conduction element 22, and the distance sensing element 23 is correspondingly installed by the side of the first surface 11 or the second surface 12.

Herein, upon operating the deformation element 1 on human skins and sliding onto a predetermined position, it is possible to use an external force to vertically push or press the deformation element 1 such that it induces deformation to allow the first surface 1 or the second surface 2 to move in the vertical direction thereby reducing the distance between the first surface 11 and the distance sensing element 23, so that in case the distance sensing element 23 detects the length L of the distance reaches 1 μm or more, it triggers the audio pickup element 21 to start to receive various physiological sounds in the human body (e.g., audio signals generated by the movement of heart, lungs, internal organs or internal tissues). Moreover, the audio pickup element 21 then receives such physiological sounds and digitalizes them into an audio file to pass into the conduction element 22; subsequently, when operating once again the deformation element 1 on human skins and sliding onto the next predetermined position, the external force vertically pressing the deformation element 1 will be released so that it can restore to the original form thus canceling the operation condition for triggering the audio pickup element 21. Therefore, the physiological sounds can be received only when the external force is applied at a single point, which can greatly reduce noises generated during the operation.

Besides, referring to FIG. 1, herein it can be seen that the deformation element 1 is installed on an electronic device 3 and the conduction element 22 is also electrically connected to the control element 31 in the electronic device 3, and the control element 31 is further electrically connected to a sound playback device 4, such that the conduction element 23 can transfer the created audio file to the electronic device 3 to allow the user to use the sound playback device 4 to listen to the received audio file and manipulate the control element 31 to control the audio file for playback, storage, sound amplification, sound reduction as well as other functions, which can be applied as a stethoscope.

Figure 3B:
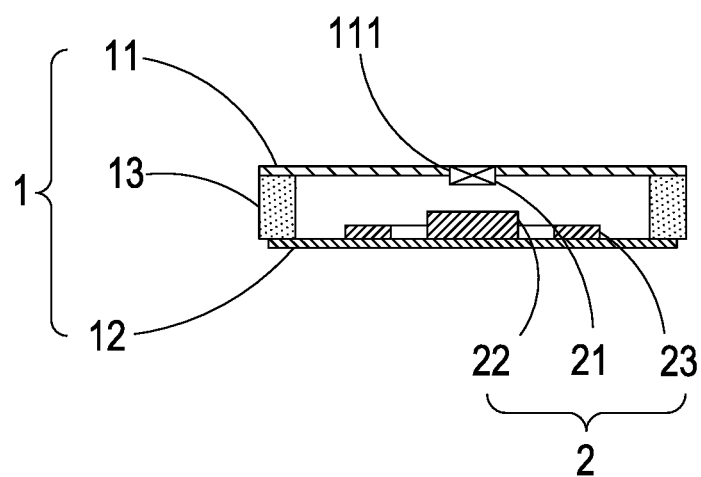
FIG. 3B shows a cross-sectioned view for the first embodiment of the deformation element in the point-pressed audio pickup apparatus according to the present invention.

Furthermore, referring to FIG. 1, it can be understood that the illustrated deformation indicates the change in the shapes of the first surface 11, the second surface 12 or the joint block 13 caused by the applied external force, e.g., extrusion, distortion, or indentation etc., which further causes the distance between the first surface 11 or the second surface 12 and the distance sensing element 23 to vary by more than 1 μm. Several embodiments according to the present invention are described as below to exemplarily illustrate a variety of possible deformation:

1. Refer to FIGS. 3A and 3B, wherein a first embodiment of the deformation element 1 is shown. In the present embodiment, the distance sensing element 23 is set up on the second surface 12 correspondingly to the first surface 11, and the joint block 13 is fabricated with the flexible materials. Therefore, when an external force vertically presses the first surface 11, the joint block 13 will be pressed by the external force to induce deformation so that the first surface 11 moves accordingly towards the distance sensing element 23 in the vertical direction thereby enabling the distance sensing element 23 to measure the amount of deformation.

Figure 4A:
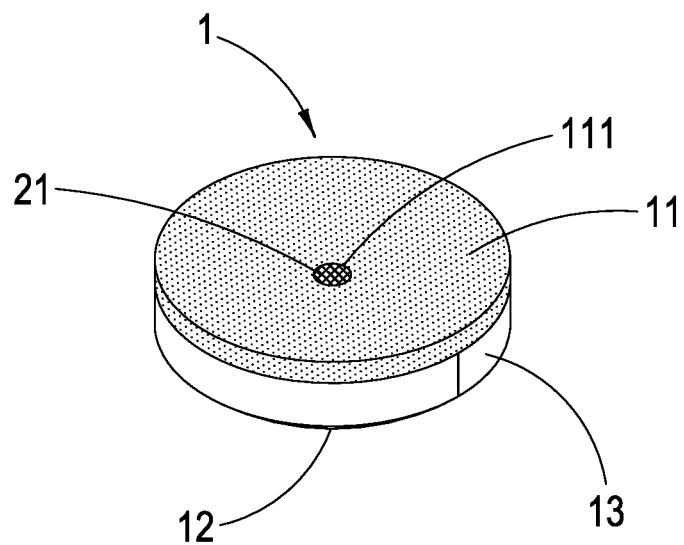
FIG. 4A shows a stereo view for a second embodiment of the deformation element in the point-pressed audio pickup apparatus according to the present invention.
Figure 4B:
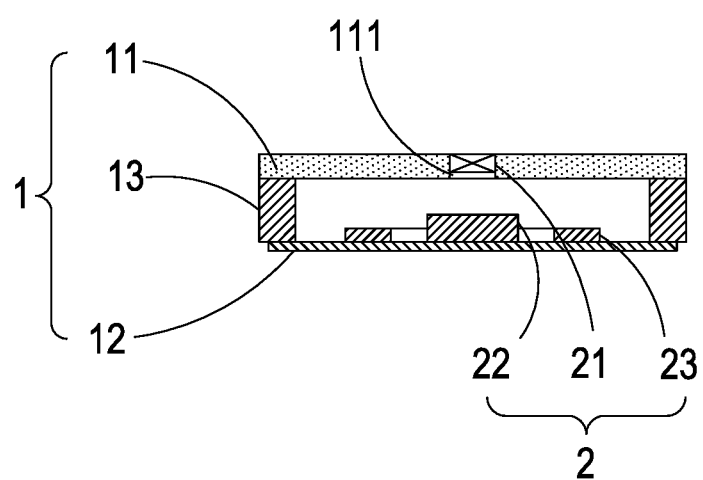
FIG. 4B shows a cross-sectioned view for the second embodiment of the deformation element in the point-pressed audio pickup apparatus according to the present invention.

2. Refer to FIGS. 4A and 4B, wherein a second embodiment of the deformation element 1 is shown. In the present embodiment, the distance sensing element 23 is set up on the second surface 12 correspondingly to the first surface 11, and the first surface 11 is fabricated with the flexible materials. Therefore, when an external force vertically presses the first surface 11, the first surface 11 will be pressed by the external force to induce deformation so that the first surface 11 moves accordingly towards the distance sensing element 23 in the vertical direction thereby enabling the distance sensing element 23 to measure the amount of deformation.

Figure 5A:
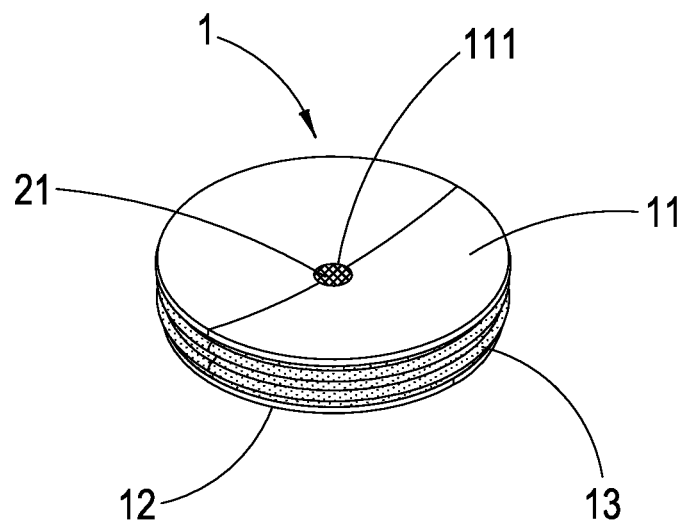
FIG. 5A shows a stereo view for a third embodiment of the deformation element in the point-pressed audio pickup apparatus according to the present invention.
Figure 5B:
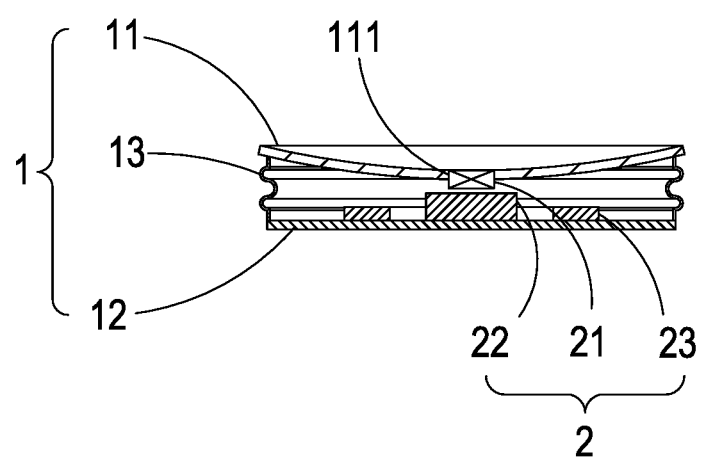
FIG. 5B shows a cross-sectioned view for the third embodiment of the deformation element in the point-pressed audio pickup apparatus according to the present invention.

3. Refer to FIGS. 5A and 5B, wherein a third embodiment of the deformation element 1 is shown. In the present embodiment, the distance sensing element 23 is set up on the second surface 12 correspondingly to the first surface 11, and the joint block 11 is designed to have continuous bumpy wave forms whose extension direction is vertical to the first surface 11 and is fabricated with flexible materials so that, when an external force is applied to press the first surface 11, the joint block 13 can be similarly pushed by the force to accordingly induce deformation.

Figure 6A:
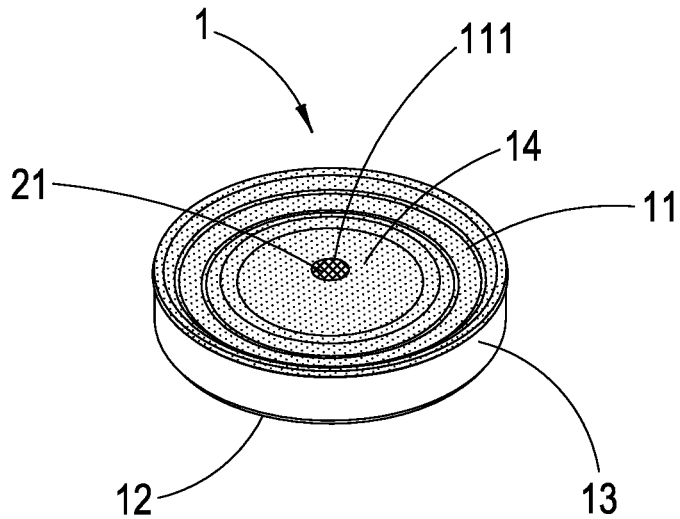
FIG. 6A shows a stereo view for a fourth embodiment of the deformation element in the point-pressed audio pickup apparatus according to the present invention.
Figure 6B:
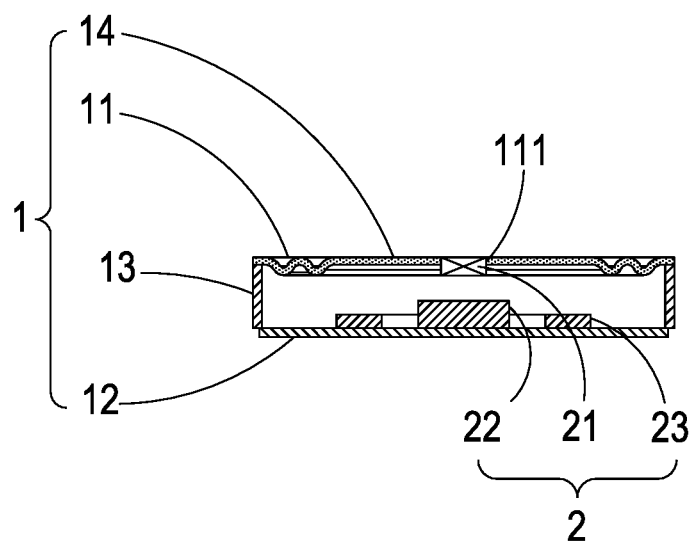
FIG. 6B shows a cross-sectioned view for the fourth embodiment of the deformation element in the point-pressed audio pickup apparatus according to the present invention.

4. Refer to FIGS. 6A and 6B, wherein a fourth embodiment of the deformation element 1 is shown. In the present embodiment, the distance sensing element 23 is set up on the second surface 12 correspondingly to the first surface 11, and the first surface 11 is designed to have continuous bumpy wave forms whose extension direction is parallel to the first surface 11; in addition, a protrusion 14 is further formed outwards on the first surface 11 and is fabricated with flexible materials so that, when an external force is vertically applied to press the first surface 11, the protrusion 14 can indent and displace in the vertical direction towards the distance sensing element 23 thereby allowing the distance sensing element 23 to measure the amount of deformation.

Figure 7A:
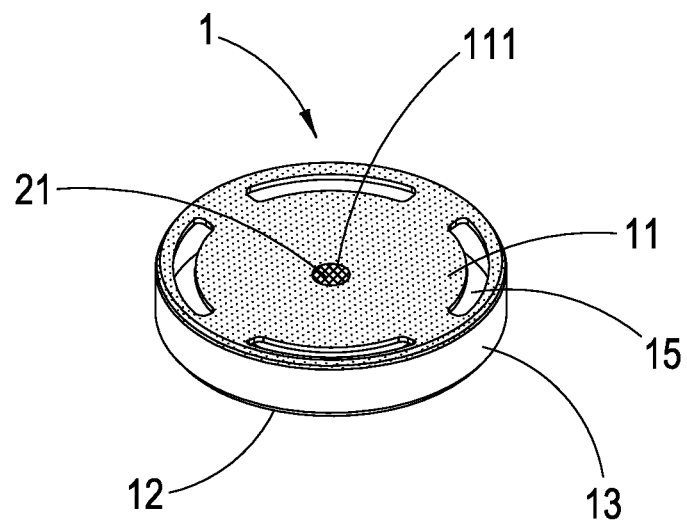
FIG. 7A shows a stereo view for a fifth embodiment of the deformation element in the point-pressed audio pickup apparatus according to the present invention.
Figure 7B:
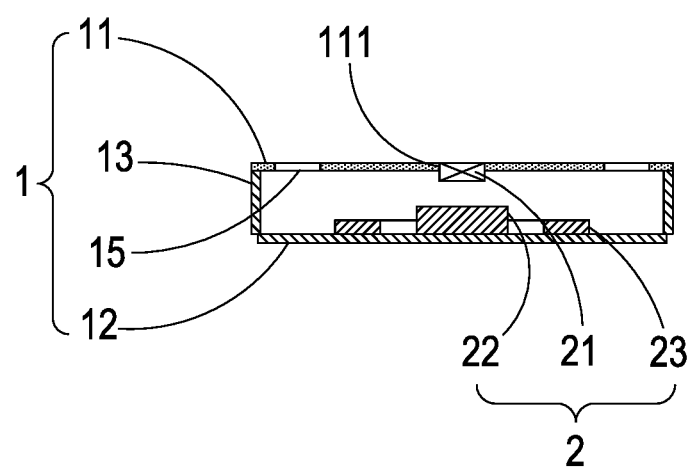
FIG. 7B shows a cross-sectioned view for the fifth embodiment of the deformation element in the point-pressed audio pickup apparatus according to the present invention.

5. Refer to FIGS. 7A and 7B, wherein a fifth embodiment of the deformation element 1 is shown. In the present embodiment, the distance sensing element 23 is set up on the second surface 12 correspondingly to the first surface 11, and plural holes 15 are evenly configured on the first surface 11 and fabricated with flexible materials; it can be seen that, since each of these holes intercepts the supportive force coming from the external periphery structure of the first surface 11 thus allowing the inner periphery of the first surface 11 to have greater deformation force, upon applying an external force to vertically press the first surface 11, the inner periphery of the surface 11 can indent and displace in the vertical direction towards the distance sensing element 23 thereby enabling the distance sensing element 23 to measure the amount of deformation.

Figure 8A:
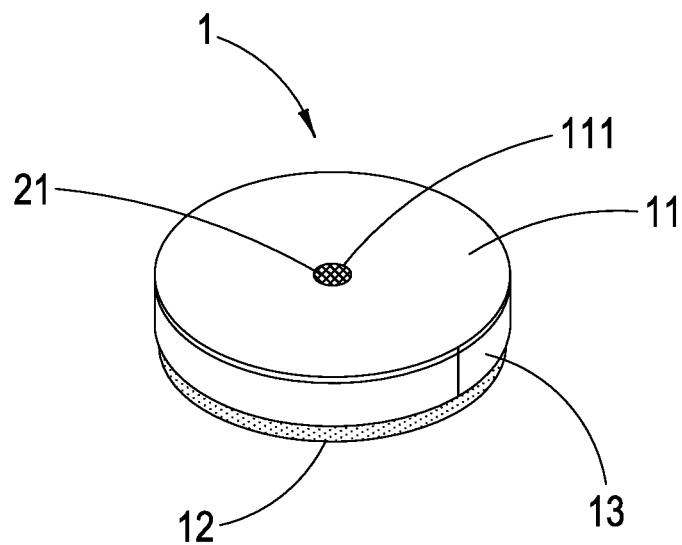
FIG. 8A shows a stereo view for a sixth embodiment of the deformation element in the point-pressed audio pickup apparatus according to the present invention.
Figure 8B:
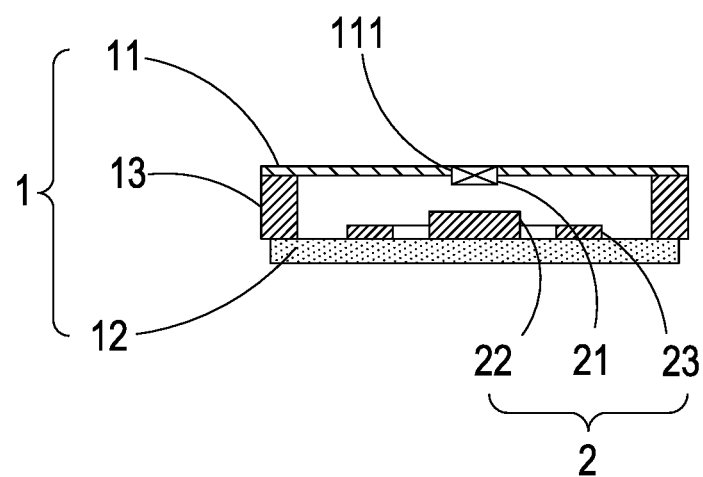
FIG. 8B shows a cross-sectioned view for the sixth embodiment of the deformation element in the point-pressed audio pickup apparatus according to the present invention.

6. Refer to FIGS. 8A and 8B, wherein a sixth embodiment of the deformation element 1 is shown. In the present embodiment, the distance sensing element 23 is set up on the second surface 12 correspondingly to the first surface 11, and the second surface 12 is fabricated with the flexible materials. Therefore, when an external force vertically presses the first surface 11, the second surface 12 will cause the distance sensing element 23 to displace in the vertical direction towards the first surface 11 thereby enabling the distance sensing element 23 to measure the amount of deformation. It should be noticed that, for the present embodiment, the first surface 11 illustrated in the second embodiment is swapped to the second surface 12 so as to achieve the same effect; analogously, the first surface 11 illustrated in the fourth and fifth embodiments can be also swapped to the second surface 12 to obtain the same feature.

Figure 9A:
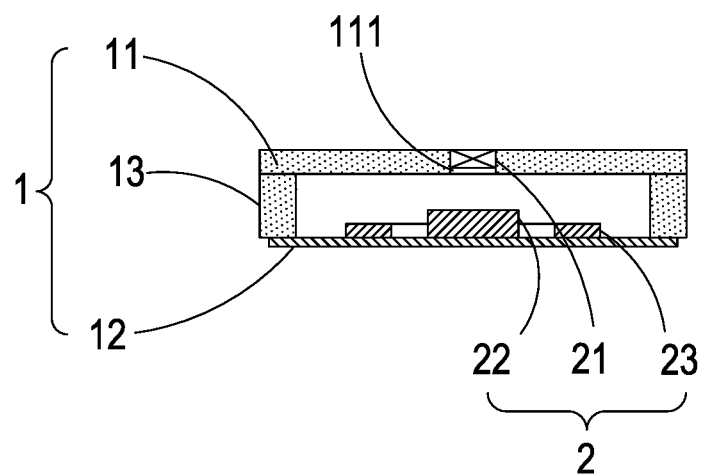
FIG. 9A shows a cross-sectioned view for a seventh embodiment of the deformation element in the point-pressed audio pickup apparatus according to the present invention.

7. Refer subsequently to FIG. 9A, wherein a seventh embodiment of the deformation element 1 is shown. It can be understood that, different from the previous first to sixth embodiments, in the present embodiment, the distance sensing element 23 is set up on the second surface 12 correspondingly to the first surface 11, and the first surface 11 as well as the joint block 13 both are fabricated with the flexible materials. Therefore, when an external force vertically presses the first surface 11, the first surface 11 will be pressed by the external force to displace in the vertical direction towards the distance sensing element 23 thereby enabling the distance sensing element 23 to measure the amount of deformation.

Figure 9B:
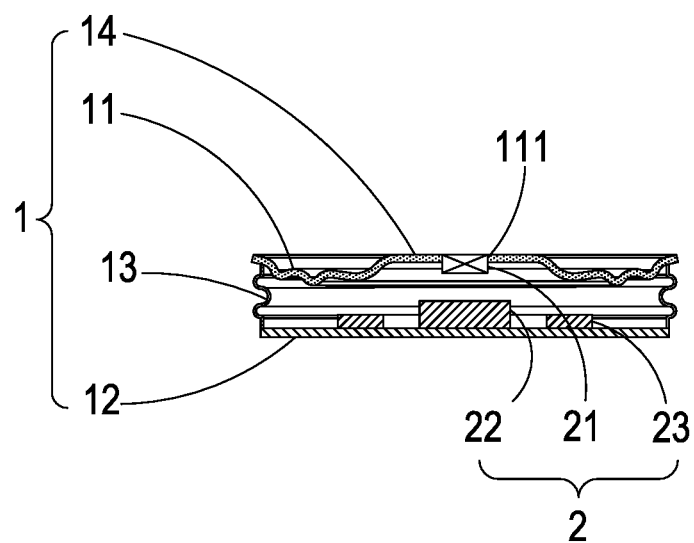
FIG. 9B shows a cross-sectioned view for an eighth embodiment of the deformation element in the point-pressed audio pickup apparatus according to the present invention.

8. Refer furthermore to FIG. 9B, wherein an eighth embodiment of the deformation element 1 is shown. In the present embodiment, the first surface 11 and the joint block 13 illustrated in the seventh embodiment are now both designed to have continuous bumpy wave forms; in addition, a protrusion 14 is further formed outwards on the first surface 11 and is fabricated with flexible materials so that, when an external force is vertically applied to press the first surface 11, the first surface 11 can displace in the vertical direction towards the distance sensing element 23 thereby allowing the distance sensing element 23 to measure the amount of deformation. Similarly, no matter be fabricated with flexible materials or designed to have continuous bumpy wave forms in the profiles, such approaches can be applied to any one or more of the first surface 11, the second surface 12 and the joint block 13 in order to achieve the same deformation performance.

The structural configurations explained in each of the aforementioned embodiments are illustrated in conjunction with the appended Figures. Additionally, it should be appreciated that, in actual applications, such configurations can be more comprehensively applied to the first surface 11, the second surface 12 or the joint block 13, rather than being restricted to what have been demonstrated in the above-said embodiments.

Moreover, the flexible materials described by the aforementioned embodiments may be silicone, rubber, soft rubber, foam, sponge, springs or other materials capable of enabling deformability and automatically returning to the original shape thereof.

The previously disclosed embodiments are merely illustrative of some preferred ones of the present invention, which are not intended to limit the scope thereof; those who are skilled in the relevant technical fields can, after understanding the technical features and embodiments of the present invention as explained hereinabove, certainly make equivalent changes, alterations or modifications without departing from the spirit and scope of the present invention, which are nonetheless deemed as falling within the coverage of the present invention; accordingly, the scope of the present invention to be protected by patent laws is subject to the definition of the claims attached to this specification.

What is claimed is:

1. A point-pressed audio pickup apparatus, comprising:
a deformation element, including a first surface, a second surface and a joint block joined between the first surface and the second surface, in which any one or more of the first surface, the second surface and the joint block can induce deformation by an external force, and an audio pickup hole is openly configured at the central position of the first surface;
an audio pickup device, including an audio pickup element installed inside the audio pickup hole, and a conduction element and a distance sensing element installed inside the deformation element, in which the audio pickup element and the distance sensing element are respectively electrically connected to the conduction element, and the distance sensing element is correspondingly installed by the side of the first surface;
wherein the first surface is attached to the surface of an object in order to push or press the deformation element by an external force vertical to the first surface to induce deformation, such that the first surface or the second surface displaces in the vertical direction thereby reducing the distance between the first surface and the distance sensing element, so that the distance sensing element can operate to measure the distance length, and the audio pickup element will be triggered to receive sound when the measured distance length reaches more than 1 μm.

2. The point-pressed audio pickup apparatus according to claim 1, wherein the deformation element is installed on an electronic device, the conduction element is also electrically connected to a control element within the electronic device, and the control element is further electrically connected to a sound playback device.

3. The point-pressed audio pickup apparatus according to claim 1, wherein the distance sensing element and the conduction element are both installed on the second surface, and the distance sensing element corresponds to the first surface.

4. The point-pressed audio pickup apparatus according to claim 1, wherein any one or more of the first surface, the second surface and the joint block are fabricated with flexible materials.

5. The point-pressed audio pickup apparatus according to claim 4, wherein the flexible materials may be silicone, rubber, soft rubber, foam, sponge, springs or other materials capable of enabling deformability and automatically returning to the original shape thereof.

6. The point-pressed audio pickup apparatus according to claim 1, wherein any one or more of the first surface, the second surface and the joint block are designed to have continuous bumpy wave forms.

7. The point-pressed audio pickup apparatus according to claim 6, wherein the first surface, the second surface or the joint block designed to have continuous bumpy wave forms are fabricated with flexible materials.

8. The point-pressed audio pickup apparatus according to claim 7, wherein the flexible materials may be silicone, rubber, soft rubber, foam, sponge, springs or other materials capable of enabling deformability and automatically returning to the original shape thereof.

9. The point-pressed audio pickup apparatus according to claim 6, wherein the first surface designed to have a continuous bumpy wave forms has a protrusion formed towards outside.

10. The point-pressed audio pickup apparatus according to claim 6, wherein the extension directions of the continuous bumpy forms of the first surface and the second surface are parallel to the first surface.

11. The point-pressed audio pickup apparatus according to claim 6, wherein the extension direction of the continuous bumpy forms of the joint block is vertical to the first surface.

12. The point-pressed audio pickup apparatus according to claim 1, wherein any one or more of the first surface or the second surface are openly configured with a plurality of holes at the same time.

13. The point-pressed audio pickup apparatus according to claim 12, wherein the first surface or the second surface openly configured with a plurality of holes are fabricated with flexible materials.

14. The point-pressed audio pickup apparatus according to claim 13, wherein the flexible materials may be silicone, rubber, soft rubber, foam, sponge, springs or other materials capable of enabling deformability and automatically returning to the original shape thereof.

* * * * *